(12) United States Patent
Forrest et al.

(10) Patent No.: US 9,770,587 B2
(45) Date of Patent: Sep. 26, 2017

(54) NEUROMUSCULAR STIMULATION SYSTEM AND METHOD

(71) Applicants: Kessler Foundation Inc., West Orange, NJ (US); The Governors of the University of Alberta, Edmonton (CA); University of Louisville, Louisville, KY (US)

(72) Inventors: Gail Florence Forrest, Cranberry, NJ (US); Susan Jill Harkema, Louisville, KY (US); David Frederic Collins, Edmonton (CA)

(73) Assignees: Kessler Foundation, Inc., West Orange, NJ (US); The Governors of the University, Edmonton (CA); University of Louisville, Louisville, KY (US)

( * ) Notice: Subject to any disclaimer, the term of this patent is extended or adjusted under 35 U.S.C. 154(b) by 0 days.

(21) Appl. No.: 14/994,613

(22) Filed: Jan. 13, 2016

(65) Prior Publication Data

US 2017/0197078 A1    Jul. 13, 2017

(51) Int. Cl.
| | | |
|---|---|---|
| *A61N 1/00* | (2006.01) | |
| *A61N 1/36* | (2006.01) | |
| *A61H 1/02* | (2006.01) | |
| *A61H 3/00* | (2006.01) | |

(52) U.S. Cl.
CPC ....... *A61N 1/36003* (2013.01); *A61H 1/0262* (2013.01); *A61H 3/008* (2013.01); *A61H 2201/10* (2013.01); *A61H 2201/1642* (2013.01); *A61H 2201/1652* (2013.01); *A61H 2203/0406* (2013.01); *A61H 2203/0431* (2013.01)

(58) Field of Classification Search
CPC .. A61N 1/36003; A61H 1/0262; A61H 3/008; A61H 2201/10; A61H 2201/1642; A61H 2201/1652; A61H 2203/0406; A61H 2203/0431
See application file for complete search history.

(56) References Cited

U.S. PATENT DOCUMENTS

| | | |
|---|---|---|
| 5,549,656 A | 8/1996 | Reiss |
| 6,615,080 B1 | 9/2003 | Unsworth et al. |
| 6,631,297 B1 | 10/2003 | Mo |
| 7,725,193 B1 * | 5/2010 | Chu .................. A61N 1/36021 607/48 |
| 8,165,685 B1 | 4/2012 | Knutson et al. |
| 8,660,651 B2 | 2/2014 | Castel et al. |
| 9,498,619 B2 | 11/2016 | Goode et al. |
| 2009/0326607 A1 | 12/2009 | Castel et al. |
| 2014/0228911 A1 | 8/2014 | Sharma et al. |

OTHER PUBLICATIONS

The International Search Report and Written Opinion, dated Apr. 12, 2017, in the related PCT Application No. PCT/US17/12813.

* cited by examiner

*Primary Examiner* — George Manuel

(57) ABSTRACT

Provided are systems and methods employing wide pulse width, high frequency, neuromuscular electrical stimulation ("WPHF-NMES") for the rehabilitation, treatment or recovery of a subject afflicted with a neuromuscular injury, disease or disorder.

20 Claims, 1 Drawing Sheet

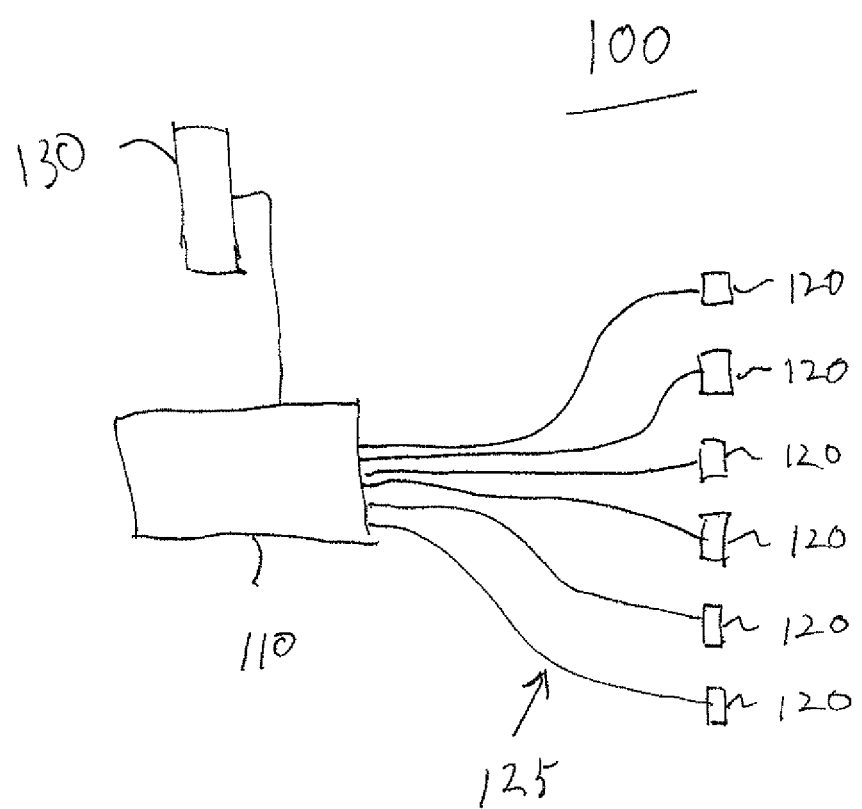

NEUROMUSCULAR STIMULATION SYSTEM AND METHOD

FIELD OF THE INVENTION

The instant invention generally relates to the field of neurological rehabilitation including traumatic and non-traumatic spinal cord injury, stroke and brain injury. Methods are provided to facilitate the recovery of posture, upper and lower limb movement and standing as well as muscle and bone loss, cardiovascular and respiratory function in a human having spinal cord injury, brain injury, or neurological disorders.

All documents cited to or relied upon below are expressly incorporated herein by reference.

BACKGROUND OF THE INVENTION

Spinal cord injury (SCI) affects thousands of individuals a year in the United States resulting in a loss of voluntary control of muscle, severe muscle atrophy and bone loss. It has been observed that six weeks after SCI, skeletal muscles below the level of the lesion decrease in cross-sectional area and begin a shift toward a fast fiber phenotype. Individuals with SCI will typically lose 50-60% of their bone mineral density (BMD) because of deterioration of the trabecular epiphyses and a thinning of the cortical wall. Owing to this rapid musculoskeletal deterioration, individuals with SCI have a 2% chance of sustaining a lower extremity fracture, which is double the fracture risk of the general population.

Neuromuscular electrical stimulation (NMES) is a method for neurological rehabilitation in patients with, among other things, SCI. NMES generates contractions by depolarising axons under stimulating electrodes placed on the skin over a muscle belly or peripheral nerve trunk. Traditionally, NMES is delivered using relatively narrow pulse widths (0.05-0.4 ms) and low frequencies (20-40 Hz). This traditional type of NMES favors the activation of motor axons and, thus, generates contractions predominantly through a peripheral pathway that does not involve the central nervous system (CNS). Accordingly, traditional NMES recruits motor units in a non-physiological manner, with a random recruitment order of motor unit types and all motor units discharge synchronously.

Traditional NMES, however, has a number of disadvantages. The random recruitment order leaves fatigue-resistant muscle fibers, those most vulnerable to developing disuse-related complications after paralysis, relatively inactive. The synchronous discharge means that all motor units discharge at the same time and, thus, discharge rates must be abnormally high to produce smooth contractions of sufficient amplitude to produce functionally meaningful contractions. Such high discharge rates increase the metabolic demand on individual motor units compared to voluntary contractions of similar amplitude. Both of these non-physiological aspects of motor unit recruitment during NMES (random recruitment order, synchronous discharge) limit the benefits and widespread use of NMES for rehabilitation.

Additionally, NMES is delivered over at least one muscle at a time, typically while participants are supine. Such a traditional NMES approach results in, for example, contractions for thighs or lower limbs rather than multi-muscle stimulation of both limbs. Further, the contractions are also unlike voluntary contractions that are produced by output from the central nervous system, thus, potentially rendering an unfavorable plateau in muscle hypertrophy. Even still, low-intensity NMES-cycling has no effect on BMD for individuals with acute or chronic SCI. High-intensity NMES-cycling, by contrast, was shown to increase BMD by approximately 10-14% at the distal femur and proximal tibia for individuals with a chronic SCI.

Thus, there exists a need in the art for NMES of multiple muscle groups, involving the central nervous system and utilizing high-intensity NMES for greater rehabilitative efficacy in patients suffering from a neuromuscular injury, disease or disorder that results in paralyses. In addition, the NMES will be combined with functional tasks such as trunk extension and the sit to stand activities.

SUMMARY OF THE INVENTION

The present invention is directed to a method for the rehabilitation, treatment or recovery of a subject afflicted with a neuromuscular injury, disease or disorder employing a stimulator for generating NMES wherein the NMES is characterized by having a wide-pulse width and at high frequency. Such wide pulse width, high frequency, NMES is referred to herein as "WPHF-NMES". The method involves disposing surface electrodes on a subject for stimulating a plurality of muscle groups; and administering: a) multiple intervention sessions each of which comprises the combination of WPHF-NMES to the muscle groups and b) a specific physical activity regime in accordance with a protocol.

The invention is also directed to a system for the rehabilitation, treatment or recovery of a subject afflicted with a neuromuscular injury, disease or disorder. The system includes a plurality of surface electrodes; a stimulator coupled to the plurality of surface electrodes; and a controller coupled to the stimulator, wherein the controller is adapted to control the stimulator to administer simultaneously WPHF-NMES to a plurality of muscle groups in accordance with a protocol.

BRIEF DESCRIPTION OF THE FIGURE

FIG. 1 depicts an exemplary embodiment of a NMES system in accordance with invention.

DETAILED DESCRIPTION OF THE INVENTION

It is to be understood that the figures and descriptions of the present invention have been simplified to illustrate elements that are relevant for a clear understanding of the present invention, while eliminating, for the purpose of clarity, many other elements found in typical systems and arrangements. Those of ordinary skill in the art will recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art. Furthermore, the embodiments identified and illustrated herein are for exemplary purposes only, and are not meant to be exclusive or limited in their description of the present invention.

The methods and system of the invention facilitate the modulation of the electrophysiological properties of CNS circuits during a specific task. These enable the activation of CNS circuits by the combination of intentional supraspinal signals from the participant, afferent signals evoked by the NMES and sensory feedback provided by proprioceptors activated during the task. Together these signals drive plasticity of the nervous system to recover that specific motor function. Also, the consistent activation of CNS circuitry by the methods and systems of the invention provides for more torque generation of the muscles and leads to improving the secondary consequences of paralysis, such as cardiovascular and respiratory complications as well as muscle and bone loss.

The inventors discovered that torque generation of a muscle is significantly greater with WPHF-NMES than with traditional stimulation techniques. The inventors have documented recovery of arm and hand function in chronic SCI patients treated with WPHF-NMES. Further, the ability to voluntarily move the legs and trunk, as well as improved trunk stability, posture, standing and walking, has been observed in individuals both with upper and motor neuron injury utilizing the method and system of the invention.

The inventors overcame the limitations of traditional NMES by, for example, delivering the WPHF-NMES stimulation in such a way as to produce contractions via pathways through the central nervous system using surface electrodes.

When contractions are produced utilizing the methods of the invention, motor neurons are recruited synaptically, thereby reducing fatigue during voluntary contractions (orderly recruitment, asynchronous discharge). Surprisingly, until the present invention, few methods have been developed to recruit motor units synaptically, via the electrically-evoked sensory volley, during NMES. Two approaches that have had some success involve implanted electrodes that block action potentials in large motor units using high-frequency of 600 Hz (Baratta et al. 1989); or anodal NMES (Fang and Mortimer 1991). In each case, action potentials are initiated at a proximal electrode and blocked at an electrode positioned distally along the nerve trunk. These methods take advantage of the reversed motor unit recruitment order of motor axons which occurs when NMES is delivered to a nerve trunk with a cuff electrode (Gorman and Mortimer 1983). Since large motor units are more easily depolarized by externally applied currents (Blair and Erlanger 1933), large motor units are also more easily blocked at lower amplitudes of direct current, high-frequency or anodal NMES. Similarly, altering the stimulus waveform has also been shown to be effective in altering recruitment order (Gorman and Mortimer 1983; Grill and Mortimer 1995; Grill and Mortimer 1996), however, this work has been primarily conducted using nerve cuffs and the efficacy of achieving improved recruitment order and improving-fatigue-resistance of evoked contractions with such techniques has not been tested thoroughly and has largely been abandoned (Solomonow 1984). Further, such techniques are not feasible for WPHF-NMES applied using electrodes placed on the surface of the skin and, thus, teach away from the instant invention.

The inventors discovered that WPHF-NMES incorporating wider pulse durations of, for example, at least approximately 1 ms and higher frequencies of, for example, approximately, 100 Hz, which are greater than used traditionally, generates contractions via pathways that traverse the CNS. The WPHF-NMES parameters disclosed herein are, thus, designed to augment the electrically-evoked sensory volley to engage CNS circuits that control movement and produce contractions that are more fatigue-resistant and better for reducing muscle and bone atrophy and improving voluntary control of muscle than contractions generated using traditional NMES.

During an exemplary WPHF-NMES session in accordance with the invention, contractions develop via two pathways. Part of the contraction arises from the well-established peripheral pathway due to the activation of motor axons beneath the stimulating electrodes. However, additional torque develops from the activation of sensory axons which recruits motor units via pathways that travel through the CNS and back to the muscle. This occurs even when the stimulation intensity is adjusted to account for the different pulse durations (thus, overall stimulation charge) and ensure that the stimulation recruits a similar number of motor axons, i.e., similar sized M-waves. It has been confirmed that the augmented torque involves CNS circuits as the additional torque did not develop when the nerve between the stimulation site and the CNS was blocked with an anesthetic (Collins et al., 2001; Collins et al., 2002; Lagerquist et al., 2009).

The inventors discovered that WPHF-NMES generates the additional contraction because a relatively larger sensory volley is sent to the CNS than during traditional NMES. Two reasons account for this. First, sensory axons have a lower rheobase and longer strength duration time constant than motor axons due to differences in the compliment of ion channels on the two types of axons (Mogyoros et al., 1996; Burke 2007). In this way, when a given number of motor axons are stimulated, i.e., similar sized M-waves, wider pulses recruit a greater proportion of sensory axons, resulting in a greater reflexive contribution to the contraction (Panizza et al., 1989) and more torque (Lagerquist and Collins 2008; Lagerquist and Collins 2010). Secondly, the relatively high stimulus frequency of, for example, approximately, 100 Hz, sends more impulses to the CNS within a given time period than occurs during traditional NMES.

In addition, the inventors discovered that BMD is increased at the hip and knee when multi-muscle WPHF-NMES sessions are combined with a physical activity such as, for example, dynamic standing. The loading force during dynamic standing with multi-muscle WPHF-NMES can be, for example, approximately 0.7 body weight per limb. The combination of multi muscle WPHF-NMES sessions with a physical activity such as, for example, dynamic standing intervention can also increase muscle strength and muscle volume.

Physiologically, the enhanced synaptic drive generated by WPHF-NMES engages CNS circuits that control movement. In this way, WPHF-NMES recruits motoneurons synaptically and in a more physiologically-relevant manner than traditional NMES. WPHF-NMES recruits motor units according to Henneman's size principle and many motor units discharge asynchronously from one and other (Dean et al., 2014). Both of these aspects of motor unit recruitment reduce fatigue of voluntary contractions since fatigue-resistant motor units are recruited first and lower motor unit discharge are required to produce contractions at functionally relevant amplitudes. Further, WPHF-NMES increases the excitability of the pathway that mediates the voluntary command from the brain to muscle (Mang et al., 2010). NMES delivered at approximately 100 Hz, but not 50 or 200 Hz, increases the excitability of the corticospinal pathway. This influence of WPHF-NMES on the excitability CNS circuits that mediate the voluntary command may be responsible in part for the improvements in voluntary control that have been observed using this approach.

FIG. 1 depicts an exemplary system 100 in accordance with the invention useable for carrying out the methods of the invention. Referring to FIG. 1, the system 100 includes a stimulator 110 coupled by wires 125 to plurality of surface electrodes 120. A programmable or programmed controller 130 is coupled to and is configured to control the stimulator 110 to implement one or more of the WPHF-NMES sessions when the surface electrodes 120 are located on a subject for stimulating one or more muscle groups. In one embodiment, the controller 130 is adapted to control the stimulator 110 to administer simultaneously WPHF-NMES sessions to a plurality of muscle groups in accordance with a protocol. The controller 130 controls the stimulator to generate a pulse width of, for example, approximately 0.5 to 3 milliseconds or greater for a minimum of one interventional training session of WPHF-NMES to the muscle groups. In another embodiment, the interventional training session is combined with a specific physical activity regime to produce contractions at least in part via pathways through the central nervous system of the subject.

In a further embodiment, the controller 130 of the system 100 controls the stimulator 110 to generate for a WPHF-NMES session a high frequency on the order of, for example, approximately 50-150 Hz. The controller 130 further controls the stimulator 110 such that a single WPHF-NMES session comprises an initial increase in frequency from approximately DC to a high frequency such as for example 150 Hz, but preferably 100 Hz, remaining at such high frequency for a sufficient duration to produce a muscle contraction appropriate for a specific physical activity, and then optionally followed by a rest period. In another embodiment, the controller 130 controls the stimulator 110 to administer at least one of the WPHF-NMES while a loading force is applied to the subject.

It should be readily understood that any controllable stimulator capable of administering a WPHF-NMES session to a subject is useable for the stimulator 110 in accordance with the present invention. Suitable examples of stimulators usable with the present invention include, but are not limited to, those from Restorative Therapies, Inc. of Baltimore, Md. The controller 130 may be any controller capable of controlling the stimulator 110 to administer one or more WPHF-NMES sessions in accordance with the invention. Suitable examples of such a controller include, but are not limited to, a computer, processor, microcontroller located separate or within the stimulator 110.

Suitable surface electrodes useable for the electrodes 120 of the system 100 include, but at not limited to, biomedical surface electrodes, known in the art and readily available to a skilled artisan, such as, for example, surface electrodes described in U.S. Pat. Nos. 6,615,080, 7,177,705, 4,300,575 and 4,367,755, all of which are expressly incorporated by reference herein. Although the electrodes 120 in FIG. 1 are coupled to the controller 130 by wires 125, it is likewise acceptable to implement the methods and systems of the present invention using wireless electrodes in which such wireless electrodes include a receiver for receiving wireless signals from the stimulator and include a separate power source from the stimulator 110.

Although FIG. 1 depicts an exemplary configuration of a system for administering one or more WPHF-NMES sessions to a subject in accordance with the invention, it should be readily understood that any system configuration capable of administering one or more WPHF-NMES sessions to a subject is usable in accordance with the invention.

Representative Embodiments of the Invention

In one embodiment of the invention, provided is a method for rehabilitation, treatment or recovery of a subject afflicted with a neuromuscular injury, disease or disorder that results in paralyses, comprising the steps of: a) disposing on said subject surface electrodes for stimulating a plurality of muscle groups; and b) administering multiple intervention sessions each of which comprises of wide pulse width, high frequency, neuromuscular electrical stimulation (WPHF-NMES) to the muscle groups. The administration of an intervention session is combined with a specific physical activity regime. "Subject" as herein defined includes a human or other animal in need of such WPHF-NMES treatment sessions. In one embodiment, the subject is a human. In another embodiment of the invention, the human suffering from a neuromuscular affliction is a quadriplegic, paraplegic or hemiplegic.

In one embodiment, the wide pulse width employed in a WPHF-NMES session is, for example, from approximately 0.5 to 3 milliseconds. In certain embodiments of the invention, the wide pulse width can be 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9 and 3.0 milliseconds or combinations thereof.

The employed frequency in the WPHF-NMES session is, for example, in the range of approximately 50 to 150 Hz. In certain embodiments, the high frequency can be 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 and 150 Hz or combinations thereof.

A WPHF-NMES session produces contractions at least in part via pathways through the central nervous system of the subject. A single session of WPHF-NMES can include, e.g., an initial increase in frequency from a low frequency to the high frequency, then remaining at this high frequency to produce a muscle contraction appropriate for the specific physical activity. In another embodiment, the WPHF-NMES session may further include one or more rest periods. In one embodiment, the low frequency is less than 5 Hz. In another embodiment, the low frequency is direct current (DC).

In a further embodiment of the invention, the number of intervention sessions are administered until a target level of recovery is achieved. The target level depends on a number of clinical factors such as, for example, the type of injury that resulted in paralysis, the extent of the injury, the age of the subject and other physiological parameters. For example, the neuromuscular injury, disease or disorder results in paralyses can be a traumatic and/or non-traumatic spinal cord injury, stroke or brain injury.

As mentioned above, the WPHF-NMES intervention can be combined with a physical activity regime common in the neuro-rehabilitative arts. In one embodiment, more than one specific physical activity is administered. The physical activity can be, without limitation, standing, sitting, sit-to-stand transitioning, walking, weight-bearing, flexing a body part or extending a body part or a combination thereof. In one embodiment, standing can be dynamic standing or standing suspended in a harness, optionally over a treadmill.

The method of the invention can also include, for example, applying a loading force to the subject during the interventional sessions. An example of a loading force includes a compressive force running parallel to the long axis of the bone.

The inventors unexpectedly discovered that recovery comprises an increase in the force generated by the muscle or a decrease in contraction-fatigue, during voluntary or electrically-evoked contractions in the subject. Thus, in one embodiment of the invention, the method results in a decrease in muscle or bone atrophy in the subject and an increase in voluntary control of skeletal muscles during a movement task.

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

EXAMPLES

Wide Pulse High Frequency Neuromuscular Electrical Stimulation

Surface electrodes were placed over muscles or nerves of the lower and/or upper extremities and trunk (legs, trunk, arms, hands). The stimulation was delivered in a frequency-modulated pattern using pulses with a duration equal to or greater than 1 ms and frequency of at least 100 Hz. WPHF-NMES was designed to produce contractions by activating motor and sensory axons, the latter of which activated spinal and other circuits in the central nervous system that control movement.

The temporal parameters of the stimulation were synchronized with the specific motor task being targeted for recovery. WPHF-NMES was combined with training of specific tasks of daily living, as detailed below, to improve motor function to levels that are representative of pre-injury or normal activity with limited use of compensatory movements.

Dynamic Stand Retraining Combined with WPHF-NMES

The objective was to facilitate dynamic weight bearing and increase the activation of the muscles of standing while at the same time enhancing the activation of spinal and other circuits in the central nervous system that control movement. The major muscle groups of both legs and trunks were stimulated simultaneously using surface electrodes placed over muscles or nerves of the lower limbs and trunk. The stimulation was delivered in a frequency-modulated pattern using pulses with a duration equal to or greater than 1 ms and frequency of at least 100 Hz. WPHF-NMES was designed to produce contractions by activating motor and sensory axons, the latter of which activated spinal and other circuits in the central nervous system that control movement. Muscles stimulated included the triceps surae, tibilias anterior, quadriceps femoris, hamstrings, gluteus maximus and erector spinae.

Participants were standing in a dynamic standing frame or standing suspended in a harness by an overhead cable (e.g., body weight support) over a treadmill. Other devices that assisted with balance were used when needed. The dynamic standing protocol was aimed at restoring stable control as in normal standing and involved practicing a series of dynamic movements repetitively while standing. A therapist or other trainers provided manual assistance as needed using specific techniques that will promote the desired motor pattern to facilitate the task.

Sit to Stand Combined with WPHF-NMES

The objective was to transition from a sit to stand position with kinematics at trunk, pelvis and legs that are as close as possible to pre-injury levels. Major muscles of the legs, pelvis and trunk were stimulated using WPHF-NMES in a temporal sequence to facilitate sit to stand. The stimulation was delivered in a frequency-modulated pattern using pulses with a duration equal to or greater than 1 ms and frequency of at least 100 Hz. WPHF-NMES was designed to produce contractions by activating motor and sensory axons, the latter of which activated spinal and other circuits in the central nervous system that control movement. Muscles stimulated included the triceps surae, tibilias anterior, quadriceps femoris, hamstrings, gluteus maximus and erector spinae.

Trunk Extension in Sitting Combined with WPHF-NMES

The major muscle groups of the trunk were stimulated in a sequential temporal pattern for trunk extension while seated. The stimulation was delivered in a frequency-modulated pattern using pulses with a duration equal to or greater than 1 ms and frequency of at least 100 Hz. WPHF-NMES was administered to produce contractions by activating motor and sensory axons, the latter of which activated spinal and other circuits in the central nervous system that control movement. The major muscle groups of trunk were stimulated simultaneously using surface electrodes placed over motor points on the muscles of the trunk. The muscles stimulated included the abdominals, upper and lower erector spinae, and trapezius.

Overhead Press Combined with WPHF-NMES

Muscles of each arm and trunk were stimulated in the sequential pattern appropriate for an overhead press movement. Surface electrodes were placed over the muscles or nerves of the trunk and arms. The stimulation was delivered in a frequency-modulated pattern using pulses with a duration equal to or greater than 1 ms and frequency of at least 100 Hz. WPHF-NMES was designed to produce contractions by activating motor and sensory axons, the latter of which activated spinal and other circuits in the central nervous system that control movement.

The invention is further described by the following numbered paragraphs:

1. A method for rehabilitation, treatment or recovery of a subject afflicted with a neuromuscular injury, disease or disorder that results in paralysis, comprising the steps of:
    a) disposing on said subject surface electrodes for stimulating a plurality of muscle groups; and
    b) administering multiple intervention sessions each of which comprises the combination of wide pulse width, high frequency, neuromuscular electrical stimulation (WPHF-NMES) to said muscle groups with a specific physical activity regime.
2. The method according to paragraph 1, wherein said wide pulse width is 0.5 to 3 milliseconds.
3. The method according to paragraph 1, wherein said high frequency is 50 to 150 Hz.
4. The method according to paragraph 1, wherein said WPHF-NMES produces contractions at least in part via pathways through the central nervous system of said subject.
5. The method according to paragraph 1, wherein a single session of WPHF-NMES comprises an initial increase in frequency from a low frequency to the high frequency of 50 to 150 HZ, remaining at this high frequency to produce a muscle contraction appropriate for the specific physical activity.
6. The method according to paragraph 5, wherein the low frequency is less than 5 Hz.

7. The method according to paragraph 6, wherein the low frequency is DC.
8. The method according to paragraph 1, wherein the number of intervention sessions are administered until a target level of recovery is achieved.
9. The method according to paragraph 1, wherein said neuromuscular injury, disease or disorder resulting in paralysis is traumatic and/or non-traumatic spinal cord injury, stroke or brain injury.
10. The method according to paragraph 1, wherein more than one specific physical activity is administered.
11. The method according to paragraph 1, wherein said physical activity is standing, sitting, sit-to-stand transitioning, walking, weight-bearing, flexing a body part or extending a body part or a combination thereof.
12. The method according to paragraph 11, wherein said standing is dynamic standing or standing suspended in a harness.
13. The method according to paragraph 1, further comprising the step of applying a loading force to said subject during said interventional sessions of a combination of WPHF-NMES to said muscle groups with a specific physical activity regime.
14. The method according to paragraph 1 and 8, wherein said recovery comprises an increase in the force generated by the muscle or a decrease in contraction-fatigue, during voluntary or electrically-evoked contractions in said subject.
15. The method according to paragraph 1, wherein recovery is a decrease in muscle or bone atrophy in said subject.
16. The method according to paragraph 1, wherein said subject is a human.
17. The method according to paragraph 16, wherein said human is a quadriplegic, paraplegic or hemiplegic.
18. A system for rehabilitation, treatment or recovery of a subject afflicted with a neuromuscular injury, disease or disorder that results in paralysis and comprising of:
    a) a plurality of surface electrodes;
    b) a stimulator coupled to the plurality of surface electrodes; and
    c) a controller coupled to the stimulator, wherein the controller is configured to control the stimulator administer simultaneously WPHF-NMES sessions to a plurality of muscle groups in accordance with a protocol.
19. The system according to paragraph 18, wherein the controller is configured to control the stimulator to generate a pulse width of 0.5 to 3 milliseconds or greater for a minimum of one interventional training session of WPHF-NMES to said muscle groups combined with a specific physical activity regime to produce contractions at least in part via pathways through the central nervous system of said subject.
20. The system according to paragraph 19, wherein said controller is configured to control the stimulator to generate a high frequency on the order of 50-150 Hz.
21. The system according to paragraph 19, wherein said controller is configured to control the stimulator such that a single session of WPHF-NMES comprises an initial increase in frequency from DC to 150 Hz, remaining at this high frequency to produce a muscle contraction appropriate for a specific physical activity.
22. The system according to paragraph 18, wherein said controller is configured to control the stimulator to administer at least one of the WPHF-NMES while a loading force is applied to said subject.

REFERENCES

Baratta, R., Ichie, M., Hwang, S. K., and Solomonow, M. (1989). Orderly stimulation of skeletal muscle motor units with tripolar nerve cuff electrode. *IEEE Trans Biomed Eng* 36, 836-843

Blair, E. A. and Erlanger, J. (1933). A comparison of the characteristics of axons through their individual electrical responses. *American Journal of Physiology* 106, 524-564.

Burke, D. (2007). The properties of axons differ according to their function. *J Physiol* 578, 1-2.

Collins, D. F., Burke, D., and Gandevia, S. C. (2001). Large involuntary forces consistent with plateau-like behavior of human motoneurons. *J. Neurosci.* 21, 4059-4065.

Collins, D. F., Burke, D., and Gandevia, S. C. (2002). Sustained contractions produced by plateau-like behaviour in human motoneurones. *J. Physiol* 538, 289-301.

Dean, J. C., Clair-Auger, J. M., Lagerquist, O., and Collins, D. F. (2014). Asynchronous recruitment of low-threshold motor units during repetitive, low-current stimulation of the human tibial nerve. *Front Hum Neurosci* 8, 1002.

Fang, Z. P. and Mortimer, J. T. (1991). A method to effect physiological recruitment order in electrically activated muscle. *IEEE Trans. Biomed. Eng* 38, 175-179.

Gorman, P. H. and Mortimer, J. T. (1983). The effect of stimulus parameters on the recruitment characteristics of direct nerve stimulation. *IEEE Trans Biomed Eng* 30, 407-414.

Grill, W. M. and Mortimer, J. T. (1995). Stimulus waveforms for selective neural stimulation. *IEEE Eng Med. Biol. Mag.* 1995, 375-385.

Grill, W. M. and Mortimer, J. T. (1996). The effect of stimulus pulse duration on selectivity of neural stimulation. *IEEE Transactions on Bio-medical Engineering* 43, 161-166.

Lagerquist, O. and Collins, D. F. (2008). Stimulus pulse-width influences H-reflex recruitment but not H(max)/M(max) ratio. *Muscle & Nerve* 37, 483-489.

Lagerquist, O. and Collins, D. F. (2010). Influence of stimulus pulse width on M-waves, H-reflexes, and torque during tetanic low-intensity neuromuscular stimulation. *Muscle Nerve* 42, 886-893.

Lagerquist, O., Walsh, L. D., Blouin, J. S., Collins, D. F., and Gandevia, S. C. (2009). Effect of a peripheral nerve block on torque produced by repetitive electrical stimulation. *Journal of Applied Physiology* 107, 161-167.

Mang, C. S., Lagerquist, O., and Collins, D. F. (2010). Changes in corticospinal excitability evoked by common peroneal nerve stimulation depend on stimulation frequency. *Exp Brain Res* 203, 11-20.

Mogyoros, I., Kiernan, M. C., Gracies, J. M., and Burke, D. (1996). The effect of stimulus duration on the latency of submaximal nerve volleys. *Muscle Nerve* 19, 1354-1356.

Panizza, M., Nilsson, J., and Hallett, M. (1989). Optimal stimulus duration for the H reflex. *Muscle Nerve* 12, 576-579.

Solomonow, M. (1984). External control of the neuromuscular system. *IEEE Trans Biomed Eng* 31, 752-763.

It is to be understood that the invention is not limited to the particular embodiments of the invention described above, as variations of the particular embodiments may be made and still fall within the scope of the appended claims.

The invention claimed is:
1. A method for rehabilitation, treatment or recovery of a subject afflicted with a neuromuscular injury, disease or disorder that results in paralysis, comprising the steps of:

a) disposing on said subject surface electrodes for stimulating a plurality of muscle groups; and
b) administering multiple intervention sessions each of which comprises the combination of wide pulse width, high frequency, neuromuscular electrical stimulation (WPHF-NMES) to said muscle groups with a specific physical activity regime, wherein a single session of WPHF-NMES comprises an initial increase in frequency from a low frequency to the high frequency and wherein the low frequency is DC.

2. The method according to claim 1, wherein said wide pulse width is 0.5 to 3 milliseconds.

3. The method according to claim 1, wherein said high frequency is 50 to 150 Hz.

4. The method according to claim 1, wherein said WPHF-NMES produces contractions at least in part via pathways through the central nervous system of said subject.

5. The method according to claim 1, wherein a single session of WPHF-NMES comprises an initial increase in frequency from a low frequency to the high frequency of 50 to 150 HZ, remaining at this high frequency to produce a muscle contraction appropriate for the specific physical activity.

6. The method according to claim 5, wherein the low frequency is less than 5 Hz.

7. The method according to claim 1, wherein the number of intervention sessions are administered until a target level of recovery is achieved.

8. The method according to claim 1, wherein said neuromuscular injury, disease or disorder resulting in paralysis is traumatic and/or non-traumatic spinal cord injury, stroke or brain injury.

9. The method according to claim 1, wherein more than one specific physical activity is administered.

10. The method according to claim 1, wherein said specific physical activity regime is standing, sitting, sit-to-stand transitioning, walking, weight-bearing, flexing a body part or extending a body part or a combination thereof.

11. The method according to claim 10, wherein said standing is dynamic standing or standing suspended in a harness.

12. The method according to claim 1, further comprising the step of applying a loading force to said subject during said interventional sessions of a combination of WPHF-NMES to said muscle groups with a specific physical activity regime.

13. The method according to claim 1 or 7, wherein said recovery comprises an increase in the force generated by the muscle or a decrease in contraction-fatigue, during voluntary or electrically-evoked contractions in said subject.

14. The method according to claim 1, wherein recovery is a decrease in muscle or bone atrophy in said subject.

15. The method according to claim 1, wherein said subject is a human.

16. The method according to claim 15, wherein said human is a quadriplegic, paraplegic or hemiplegic.

17. A system for rehabilitation, treatment or recovery of a subject afflicted with a neuromuscular injury, disease or disorder that results in paralysis and comprising of:
a) a plurality of surface electrodes;
b) a stimulator coupled to the plurality of surface electrodes; and
c) a controller coupled to the stimulator, wherein the controller is configured to control the stimulator administer simultaneously WPHF-NMES sessions to a plurality of muscle groups in accordance with a protocol, and wherein said controller is configured to control the stimulator such that a single session of WPHF-NMES comprises an initial increase in frequency from DC to 150 Hz, remaining at this high frequency to produce a muscle contraction appropriate for a specific physical activity.

18. The system according to claim 17, wherein the controller is configured to control the stimulator to generate a pulse width of 0.5 to 3 milliseconds or greater for a minimum of one interventional training session of WPHF-NMES to said muscle groups combined with a specific physical activity regime to produce contractions at least in part via pathways through the central nervous system of said subject.

19. The system according to claim 18, wherein said controller is configured to control the stimulator to generate a high frequency on the order of 50-150 Hz.

20. The system according to claim 17, wherein said controller is configured to control the stimulator to administer at least one of the WPHF-NMES while a loading force is applied to said subject.

* * * * *